US005922302A

United States Patent [19]

Goldenberg et al.

[11] Patent Number: 5,922,302

[45] Date of Patent: Jul. 13, 1999

[54] DETECTION AND THERAPY OF LESIONS WITH BIOTIN/AVIDIN-METAL CHELATING PROTEIN CONJUGATES

[75] Inventors: David Milton Goldenberg, Short Hills; Gary L. Griffiths, Morristown; Hans J. Hansen, Mystic Island, all of N.J.

[73] Assignee: Immunomedics, Inc., Morris Plains, N.J.

[21] Appl. No.: 08/440,652

[22] Filed: May 15, 1995

Related U.S. Application Data

[63] Continuation of application No. 08/409,960, Mar. 23, 1995, Pat. No. 5,736,119, which is a continuation of application No. 08/062,662, May 17, 1993, abandoned.

[51] Int. Cl.[6] ........................... A61K 51/00; C07K 16/00

[52] U.S. Cl. ........................ 424/1.41; 424/1.45; 424/9.2; 424/9.3; 424/9.34; 530/367; 530/400; 530/402; 530/391.3; 548/303.7

[58] Field of Search .................................... 530/400, 402, 530/367, 391.3, 391.5; 548/303.7; 424/1.53, 1.43, 1.45, 1.81, 9.2, 9.3, 9.34

[56] References Cited

U.S. PATENT DOCUMENTS

| | | | |
|---|---|---|---|
| 4,782,840 | 11/1988 | Martin, Jr. et al. | 128/654 |
| 4,863,713 | 9/1989 | Goodwin et al. | 424/1.79 |
| 4,932,412 | 6/1990 | Goldenberg | 128/654 |
| 5,443,813 | 8/1995 | Hainfeld | 424/1.53 |
| 5,482,698 | 1/1996 | Griffiths | 424/1.45 |
| 5,525,338 | 6/1996 | Goldenberg . | |

FOREIGN PATENT DOCUMENTS

| | | |
|---|---|---|
| 496 074 | 7/1992 | European Pat. Off. . |
| 93/25240 | 12/1993 | WIPO . |

OTHER PUBLICATIONS

D.J. Hnatowich et al., "Improved Tumor Localization with (Strept)avidin and Labeled Biotin as a Substitute for Antibody" 2211b Nuclear Medicine and Biology, vol. 20, pp. 189–195 (1993).

Leslie A. Khawli et al., "Improved Immunotargeting of Tumors with Biotinylated Monoclonal Antibodies and Radiolableled Streptavidin" Antibody, Immunoconjugates, and Radiopharmaceuticals, vol. 6, No. 1, pp. 13–27 (1993).

G. Pagtanelli et al., "Three–Step Monoclonal Antibody Tumor Targeting in Carcinoembryonic Antigen–positive Patients" Cancer Research 51, pp. 5960–5966 (1991).

Goodwin, D. A. et al., "Pre–Targeted Immunoscintigraphy of Murine Tumors with Indium–111–Labeled Bifunctional Haptens", *The Journal of Nuclear Medicine*, 29:226–234 (1988).

Hnatowich, D. J. et al., "Investigations of Avidin and Biotin for Imaging Applications", *The Journal of Nuclear Medicine*, 28:1294–1302 (1987).

Oehr, P. et al., "Streptavidin and Biotin as Potential Tumor Imaging Agents", *The Journal of Nuclear Medicine*, 29:728–729 (May 1988).

Klibanov, A. L. et al., "Blood Clearance of Radiolabeled Antibody: Enhancement by Lactosamination and Treatment with Biotin–Avidin or Anti–Mouse IgG Antibodies", *The Journal of Nuclear Medicine*, 29: No. 12, 1951–1956 (Dec. 1988).

Sinitsyn, V. V. et al., "Rapid Blood Clearance of Biotinylated IgG After Infusion of Avidin", *The Journal of Nuclear Medicine*, 30:66–69 (1989).

Schechter, B. et al., "Indirect Immunotargeting of CIS–PT to Human Epidermoid Carcinoma KB Using the Avidin–Biotin System", *Int. J. Cancer*:48, 167–172 (1991).

Paganelli, G. et al., "Three–Step Monoclonal Antibody Tumor Targeting in Carcinoembryonic Antigen–positive Patients", *Cancer Research 51*, 5960–5966 (Nov. 1991).

Paganelli, G. et al., "Monoclonal Antibody Pretargetting Techniques for Tumour Localization: The Avidin–biotin System", *Nuclear Medicine Communications 12*, 211–234 (1991).

Stickney, D. R., "Bifunctional Antibody: A Binary Radiopharmaceutical Delivery System for Imaging Colorectal Carcinoma", *Cancer Research 51*, 6650–6655 (Dec. 15, 1991).

(List continued on next page.)

*Primary Examiner*—Ponnathapura Achutamurthy
*Assistant Examiner*—P. Ponnaluri
*Attorney, Agent, or Firm*—Foley & Lardner

[57] ABSTRACT

Improved methods of detecting and/or treating lesions in a patient are provided. The improved methods comprise the steps of (a) parenterally injecting a subject with a targeting composition comprised of a conjugate of biotin and targeting protein or of an avidin and targeting protein, wherein the targeting protein preferentially binds to a marker substance produced or associated with the targeted lesion, and allowing the targeting protein conjugate to preferentially accrete at the targeted lesion; (b) then parenterally injecting a clearing composition comprised of (i) avidin, when the targeting composition is a biotin-targeting protein conjugate, or (ii) biotin, when the targeting composition is a avidin-targeting protein conjugate, and allowing the clearing composition to substantially clear the targeting composition from non-targeted sites and to bind to the targeting composition accreted at the targeted lesion; (c) parenterally injecting a localization agent which may be the same or different form the clearing agent; (d) parenterally injecting a detection or therapeutic composition comprised of a conjugate of (i) avidin and naturally occurring metal-ion chelating protein chelated with chelatable metal detection or therapeutic agent when the clearing composition is biotin, or (ii) biotin and naturally occurring metal-ion carry protein chelated with chelatable a metal detection or therapeutic agent when the clearing agent is avidin, and allowing the composition to accrete at the targeted lesion. The improvement is that the use of the chelating protein to chelate a chelatable metal therapeutic or detection agent amplifies the amount of detection or therapeutic agent at the targeted site.

36 Claims, No Drawings

OTHER PUBLICATIONS

Yuan, Fan, "Pharmacokinetic Analysis of Two–Step Approaches Using Bifunctional and Enzyme–conjugated Antibodies", *Cancer Research 51*, 3119–3130 (Jun. 15, 1991).

Paganelli, G., "In Vivo Labelling of Biotinylated Monoclonal Antibodies by Radioactive Avidin: A Strategy to Increase Tumor Radiolocalization", *Int. J. Cancer*: Supplement 2, 121–125 (1988).

Kalofonos, H. P. et al., "Imaging of Tumor in Patients with Indium–111–Labeled Biotin and Streptavidin–Conjugated Antibodies: Preliminary Communication", Journal of Nuclear Medicine, 31:1791–1796 (1990).

Paganelli, P. et al., "Tumor Targeting in Patients with Ovarian Cancer Using Biotinylated Monoclonal Antibodies and Radioactive Streptavidin", Scientific Papers, Proceedings of the 37th Annual Meeting, vol. 31, No. 5 (May 1990).

Hainfeld, J. F., "Uranium–loaded Apoferritin with Antibodies Attached: Molecular Design for Uranium Neutron–capture Therapy", *Proc. Natl. Acad. Sci. USA*, vol. 89, 11064–11068 (Nov. 1992).

Osband, et al., Immunol. Today, 11:193, 1990.

V. Hird, et al., "Immunotherapy with Monoclonal Antibodies", Genes and Cancer, 1990, pp. 183–189.

Harris et al., "Therapeutic Antibodies –The Coming of Age", TIBTECH, vol. 11, 1993, pp. 42–44.

DETECTION AND THERAPY OF LESIONS WITH BIOTIN/AVIDIN-METAL CHELATING PROTEIN CONJUGATES

This application is a continuation of application Ser. No. 08/409,960, filed Mar. 23, 1995 now U.S. Pat. No. 5,736,119 which is a continuation of Ser. No. 08/062,662, filed May 17, 1993 now abandoned.

BACKGROUND OF THE INVENTION

1. Field of the Invention

The present invention relates to improved methods for detecting and treating pathological conditions with a multi-step process using compositions containing biotin and/or avidin conjugated to a naturally occurring metal-ion chelating protein.

2. Description of the Prior Art

Antibodies against different determinants associated with pathological and normal cells, as well as associated with pathogenic microorganisms, have been used for the detection and treatment of a wide variety of pathological conditions or lesions. The targeting antibody is conjugated to an appropriate detection or therapeutic agent as described, for example, in Hansen et al., U.S. Pat. Nos. 3,927,193 to Hansen et al., and 4,331.647, 4,348,376, 4,361,544, 4,468,457, 4,444,744, 4,460,459, 4,460,561, 4,624,846 and 4,818,709 to Goldenberg, the disclosure of all of which are incorporated herein by reference.

When detecting a lesion a high signal-to-background ratio needs to be achieved. Therapy also requires a high absolute accretion of the therapeutic agent in the lesion, as well as a reasonably long duration of uptake and binding. High background levels of non-targeting antibody have long been recognized as a major impediment to high target:background ratios being achieved. To overcome this impediment various methods have been developed, such as those described in the above-referenced Goldenberg patents.

Still other methods have been developed to increase the target:background ratios of the detection or therapeutic agents, such as pre-targeting and biotin/avidin approaches, as described, for example, in Goodwin et al., U.S. Pat. No. 4,863,713; Goodwin et al., *J. Nucl. Med.* 29:226, 1988; Hnatowich et al., J. Nucl. Med. 28:1294, 1987; Oehr et al., *J. Nucl. Med.* 29:728, 1988; Klibanov et al., *J. Nucl. Med.* 29:1951, 1988; Sinitsyn et al., *J. Nucl. Med.* 30:66, 1989; Kalofonos et al., *J. Nucl. Med.* 31:1791, 1990; Schechter et al., *Int. J. Cancer* 48:167, 1991; Paganelli et al., *Cancer Res.* 51:5960, 1991; Paganelli et al., *Nucl. Med. Commun.* 12:211, 1991; Stickney et al., *Cancer Res.* 51:6650, 1991; and Yuan et al., *Cancer Res.* 51:3119, 1991; all incorporated herein in their entirety by reference.

Avidin, found in egg whites, has a very high binding affinity for biotin, which is a B-complex vitamin (Wilcheck et al., *Anal. Biochem,* 171:1, 1988). Streptavidin, derived from *Streptomyces avidinii,* is similar to avidin, but has lower non-specific tissue binding, and therefore often is used in place of avidin. Both avidin and streptavidin have a tetravalency for biotin, thus permitting amplification when the former bind to biotin.

In a prior art 2-step procedure, a targeting antibody is conjugated with either avidin or biotin and then is injected into a patient, thus localizing the avidin or biotin at a tumor of interest. Thereafter, either biotin or avidin (depending on which was coupled to the targeting antibody), bearing an imaging isotope is injected and is localized at the site of the primary antibody by binding to avidin or biotin respectively.

Timing of the second injection after the first one is very critical. Injecting the radiolabeled avidin or biotin too early will increase the avidin/biotin conjugates in the bloodstream and nontargeted tissues, while injecting very late may decrease the amount targeted to the tumor because of reduced retention of the primary antibody at the tumor.

Paganelli et al. (*Int. J. Cancer* 2:121, 1988) and Kalofonos et al. (*J. Nucl. Med.* 31:1791, 1990) demonstrated the feasibility of the above approach (the former used biotinylated antibody; the latter used streptavidin-conjugated antibody for tumor localization). In work reported by Kalofonos et al. (ibid.), 3 of 10 patients showed improved imaging. However, the patients also showed that labeled biotin alone (without antibody pretargeting) could detect tumors in 8 of 10 patients.

Paganelli et al. (*J. Nucl. Med.* 31:735, 1990 and *Cancer Res.* 51:5960, 1991) disclose a 3-step approach wherein a biotinylated antibody is administered, followed by cold, i.e., non-labeled and non-conjugated, avidin to clear nontargeted antibody, and then a radiolabeled biotin is given which binds to the avidin retained in the body, presumably where the avidin has complexed to the biotinylated antibody. By this method, Paganelli et al. were able to show, with the exception of the kidneys, high tumor:normal organ ratios. Therefore, a need exists for better methods and compositions which will allow for higher and more selective targeting and retaining detection and therapeutic agents to and at pathological lesions and for retaining higher amounts of biotin with the original antibody.

OBJECTS OF THE INVENTION

The principal object of the present invention is to provide a method to deliver higher amounts and higher target:non-target ratios of detection or therapeutic agents to a targeted site.

Another object of the invention is to provide a multiple-step procedure which targets higher amounts of a detection or therapeutic agent to a lesion.

Yet another object of the invention is to provide a plurality of detection or therapeutic agents within these targeting methods.

Upon further study of the specification and appended claims, further objects and advantages of this invention will become apparent to those skilled in the art.

SUMMARY OF THE INVENTION

One embodiment of the present invention is an improvement in a method of detecting or treating lesions in a patient. The method comprising the steps of:

(a) parenterally injecting a subject with a targeting composition comprised of a conjugate of biotin and targeting protein, wherein the targeting protein preferentially binds to a marker substance produced or associated with the targeted lesion, and allowing the conjugate to preferentially accrete at the targeted lesion;

(b) then parenterally injecting at least one dose of a clearing and localizing composition comprised of avidin, and allowing the composition to substantially clear the targeting composition from non-targeted sites and to localize by binding to the targeting composition accreted at the targeted lesion;

(c) parenterally injecting a detection or therapeutic composition comprised of a conjugate of biotin and detection or therapeutic agent, and allowing the composition to accrete at the targeted lesion; and (d) using the detection or therapeutic agent to detect or treat the targeted lesion; wherein the improvement is that the conjugate of at least step (c) further comprises a naturally occurring metal-ion chelating protein capable of carrying at least four metal ions per chelating protein, thereby amplifying the amount of detection or therapeutic agent at the targeted site.

In another embodiment, the method provides another method of detecting or treating lesions in a patient. The method comprises the steps of (a) injecting a subject with a first composition comprised of a conjugate of biotin and targeting protein, wherein the targeting protein binds to a marker substance produced by or associated with the target lesion, and allowing the biotin-targeting protein conjugate to accumulate at the target lesion;

(b) injecting at least one dose of a clearing and localizing composition comprised of avidin, and allowing the avidin to remove circulating biotin-targeting protein conjugate and to bind to biotin at the target lesion;

(c) injecting a composition comprised of a conjugate of biotin, naturally occurring metal-ion chelating protein, and metal imaging or therapeutic agent, and allowing the conjugate to bind to the avidin at the targeted lesion; and (d) using the detection or therapeutic agent to detect or treat the targeted lesion.

In another embodiment, the method provides another method of detecting or treating lesions in a patient. The method comprises the steps of (a) injecting a subject with a first composition comprised of a conjugate of avidin and targeting protein, wherein the targeting protein binds to a marker substance produced by or associated with the target lesion, and allowing the avidin-targeting protein conjugate to accumulate at the target lesion;

(b) optionally, injecting a clearing agent comprised of biotin, and allowing the clearing agent to remove circulating avidin-protein conjugate;

(c) injecting a localizing composition comprised of a conjugate containing multiple biotins, and allowing the multiple biotin conjugate to bind to avidin accumulated at the target lesion;

(d) injecting a composition comprised of a conjugate of avidin, naturally occurring metal-ion chelating protein, and metal detection or therapeutic agent, and allowing the conjugate to bind to the biotin at the targeted lesion; and (e) using the detection or therapeutic agent to detect or treat the targeted lesion.

In another embodiment, the method provides another method of detecting or and treating lesions in a patient. The method comprises the steps of (a) injecting a subject with a first composition comprised of a conjugate of avidin and targeting protein, wherein the targeting protein binds to a marker substance produced by or associated with the target lesion, and allowing the avidin-targeting protein conjugate to accumulate at the target lesion;

(b) optionally, injecting a clearing agent comprised of biotin, and allowing the clearing agent to remove circulating avidin-protein conjugate;

(c) injecting a composition comprised of a conjugate of biotin, naturally occurring metal-ion chelating protein, and chelatable detection or therapeutic agent, and allowing the conjugate to bind to the avidin at the targeted lesion; and (d) using the detection or therapeutic agent to detect or treat the targeted lesion.

DETAILED DISCUSSION

It has now been found that the procedures of the present invention are more advantageous for selective detection and therapy of lesions than the methods of the prior art because of the increase in the amount of detection/therapeutic agent that is available at the targeted site due to the ability of the naturally occurring metal-ion chelating protein to enhance the amount of detection or therapeutic metal-ions available at the targeted lesion.

In a more preferred embodiment of this invention involving a 3-step approach, a biotin-targeting antibody or fragment is injected, followed by the application of avidin as a clearing and localizing agent. Then, as a third step, a conjugate of biotin-ferritin-metal ion detection or therapeutic agent is injected.

Each of these approaches is an improvement, in terms of absolute amount of detection or therapeutic agent delivered and retained at the site of the lesion, as compared to the prior art procedures which did not contemplate the use of a naturally occurring metal-ion chelating protein bearing multiple metal ions, in amplifying the amount of detection or therapeutic agents available at the targeted site.

Of course, if desired, steps in the method can be repeated for additional accumulation of the agents, as needed. Or other amplication techniques can be used so long as one of the steps includes the use of a naturally occurring metal-ion chelating polymer to increase the amount of a detection or therapeutic metal ion at the targeted site.

The preferred lesion-targeting antibody can be a bispecific or hybrid antibody, whereby at least 2 antibody arms are directed against different epitopes of the same antigen or against different substances associated with the lesion. This is preferred in order to achieve higher levels of accretion and binding in the lesion.

These methods of the present invention provide the following improved results over other sequences reported earlier by others:

1. increased absolute targeting of detection and therapeutic agent amounts to the lesion;
2. improved lesion detection or therapy; and
3. higher lesion:normal organ (including kidney) ratios;

The metal-ion detection/therapeutic agents used in the methods of the present invention can be any or multiples of detection (diagnostic) or therapeutic radionuclides (e.g., alpha-, beta-, gamma-, positron-, x-ray- and fluorescence-emitters; electron- and neutron-capturing agents; or MRI agents).

The methods of the present invention can be used to detect (either by internal procedures or by external imaging) and/or treat lesions, including cancers, infectious diseases, cardiovascular diseases and other pathological conditions.

Internal detection procedures include intraoperative, intravascular or endoscopic, including laparoscopic, techniques, both surgically invasive and non-invasive.

Naturally occurring metal-ion chelating proteins which can chelate at least 2 metal atoms, and preferably at least 7 metal atoms, are useful in the present invention. The following and other metal-binding proteins have been reviewed in "*Advanced Inorganic Chemistry*" by F. A. Cotton and G. Wilkinson, page 1310–1345, 4th edition, 1980 (publ. John Wiley, NY). Ferritin is preferred for use in the current invention because it is capable of binding up to 4300 metal atoms. However other proteins, though having lower molecular weight and lower metal ion chelating capacity than ferritin, could be used in lieu of ferritin. These proteins would be more useful with high specific activity radioisotopes.

Ferritin is an iron-storage protein. In its iron-free form (apoferritin), it is a protein of MW 444,000 which is capable of binding up to 4300 iron atoms in the ferric (3+) state such that 1 mg of protein can bind 0.21 mg of metal. Its function is iron storage in cells, and it is found in high concentrations in liver, spleen and bone marrow. The amount of ferritin in circulation in serum normally varies between 10 and 200 ng/mL. Research grade material is obtained from horse spleen. The gross weight of the ferritin unit when fully loaded with iron is almost 900,000. The protein sheath is made up of 24 identical sub-units of 163 amino-acids each (sub-unit MW+18.5 kD) with each sub-unit approximating a cylinder 27 Å in diameter and 54 Å in length. The entire iron-loaded structure is approximately spherical with a diameter of nearly 120 Å (12.5 nm in diameter with a central cavity of about 8.0 nm).

Ferritin is especially useful in carrying a very large number of metal ions as required in MRI, neutron capture therapy or when using carrier-added radionuclides.

Metallothioneins are also described in *Metallothioneins: Proceedings of the First International Meeting on Metallothionein and Other Low Molecular Weight Metal-Binding Proteins,* Zurich, Jul. 17–22, 1978, ed. by Kagi and Norberg, Birkhause Verlag Basel, 1979 (hereinafter Kagi and Norberg). Pages 46–92 of Kagi and Norberg are incorporated herein by reference and summarized below. Metallothionein was discovered in 1957; the cadmium and the zinc containing protein isolated from equine kidney. Substantially the same protein was later found in rabbits, humans, monkeys, cattle, pigs, dogs, hamsters, rats, mice and seals. Equine metallothionein was characterized as having: molecular weight of 6000–7000: high metal content; high cysteine content; no aromatic amino acid; optical features of metal thiolates (mercaptides) and fixed distribution of cysteinyl residues. It was agreed by the plenum of the First International Meeting on Metallothioneins, referred to above, that proteins resembling equine renal metallothionein in several of these features can be designated as "metallothionein" (Kagi and Nordberg, p. 48), and this is the manner in which the term is used in this specification. Of course, metallothionein fragments are also useful in the practice of this invention as are functionally similar polypeptides having at least about six amino acid residues.

Generally speaking, metallothioneins are low molecular weight proteins which are produced in vivo and which chelate a wide variety of metal ions with high affinity. The physiological function of metallothioneins is not well-understood, but it is generally accepted that they function in the homeostasis of essential metals and the detoxification of heavy metals. Metallothioneins are ubiquitous to the higher vertebrates, invertebrates, and eukaryotic and prokaryotic microorganisms. Exposure of the many organisms to metal ions of e.g., cadmium, mercury, zinc or copper induces rapid de novo synthesis of metallothioneins by enhanced production of the mRNA for azoprotein thionein. Therefore, molecules such as cadystin, produced by certain microrganism in response to cadmium injection are also included in the scope of the present invention.

All mammalian thioneins contain [cysteine] amino-acid residues and can bind 7 gram-atoms of divalent or up to 10 gram-atoms of monovalent metal ion per mole. Thioneins contain no aromatic or histidine residues, and 20 of the amino acid residues in mammalian thioneins are cysteines.

Because the sulfhydryl moieties in the metallothioneins are bound to metal ions, they are generally not available to serve as functional groups for conjugation to targeting proteins, but other groups, such as —$NH_2$, —OH and —COOH groups are available, and the metallothioneins can thus be covalently conjugated to targeting proteins using reagents and methods which utilize these groups, while essentially not interfering in the protein's metal-binding capability.

Metals which can be chelated by metallothionein include many diagnostic and therapeutic radionuclides. Diagnostic radionuclides include Ruthenium-95, Ruthenium-97, Ruthenium-103, Ruthenium-105, Technetium-99m, Mercury-197, Gallium-67, Gallium-68, Osmium-191, Indium-Ill, Indium 113m and Lead-203. Therapeutic radionuclides include Palladium-103, Palladium-109, Silver-I1, Antimony-119, Actinium225, Gold-198, Gold-199, Copper-67, Rhenium-186, Rhenium-188, Rhenium-189, Leads 212 and Bismuth-212.

Metallothionein (MW 7000 and seven (7) metal ions bindable per molecule) is useful for strongly binding to reduced metallic anions such as rhenium as well as 'soft metal' cations such as cadmium, silver, mercury, copper and zinc. A "soft metal" cation is one which preferentially binds with a nitrogen or sulfur containing ligand rather than an oxygen containing ligand.

Ferredoxins are iron-sulfur proteins wherein the iron is bound to sulfur ligands. The iron is bound in sulfur clusters, usually with eight iron atoms per molecule of protein in the case of ferredoxin itself. Other sub-types of the protein may contain up to 18 atoms of iron per molecule of protein. Related proteins such as the Aztobacter molybdenum-iron protein has 32 iron atoms and 2 molybdenum atoms per unit molecular weight of 270 kD.

Nitrogenase is a bacterial/algal protein of 220 kD containing 2 molybdenum and 24 iron atoms.

Ceruloplasmin is a copper-binding plasma glycoprotein widely found in the animal kingdom. Human plasma contains 2040 mg of ceruloplasmin per 100 ml which enables the preparation of gram quantities of the protein. Ceruloplasmin has a molecular weight of 151 kD and is 0.3% copper by weight, thus 6 to 7 copper atoms per protein molecule is present. The copper can be exchanged out of the protein in vitro.

Laccase is a naturally occurring copper-binding protein which is isolated from Polyporus, a type of plant fungus. It is a copper-containing enzyme of the oxidase type containing more than four copper atoms per mole of protein.

Avidins are a family of proteins functionally defined by their ability to bind biotin with high affinity and specificity.

Avidins are fairly small oligomeric proteins, made up of four identical subunits, each bearing a single binding site for biotin. Avidins can therefore bind up to four moles of biotin per mole of avidin.

Avidins include proteins (a) produced by amphibians, reptiles and avians, which is present in their eggs and known as avidin, and (b) produced by a streptomyces, *Streptomyces avidinii*, and known as streptavidin. As used herein "avidin" includes all of the above proteins.

Targeting proteins are known which preferentially bind marker substances that are produced by or associated with lesions. For example, antibodies can be used against cancer-associated substances, as well as against any pathological lesion that shows an increased or unique antigenic marker, such as against substances associated with is cardiovascular lesions, such as, vascular clots including thrombi and emboli, myocardial infarctions and other organ infarcts, atherosclerotic plaques; inflammatory lesions; and infectious and parasitic agents. Examples of appropriate applications are provided in the above-referenced and incorporated Goldenberg patents and applications.

The cancer states include carcinomas, melanomas, sarcomas, neuroblastomas, leukemias, lymphomas, gliomas and myelomas.

The infectious diseases include those caused by invading microbes or parasites. As used herein, "microbe" denotes virus, bacteria, rickettsia, mycoplasma, protozoa, fungi and like microorganisms, "parasite" denotes infectious, generally microscopic or very small multicellular invertebrates, or ova or juvenile forms thereof, which are susceptible to antibody-induced clearance or lytic or phagocytic destruction, e.g., malarial parasites, spirochetes and the like, including helminths, while "infectious agent" or "pathogen" denotes both microbes and parasites.

The protein substances useful in the methods of the present invention include protein, peptide, polypeptide, glycoprotein, lipoprotein, or the like, e.g. hormones, lymphokines, growth factors, albumin, cytokines, enzymes, immune modulators, receptor proteins, antibodies and antibody fragments.

The protein substance of particular interest in the present invention are antibodies and antibody fragments. By "antibodies and antibody fragments" is meant generally immunoglobulins or fragments thereof that specifically bind to antigens to form immune complexes.

The antibody may be whole immunoglobulin of any class, e.g., IgG, IgM, IgA, IgD, IgE, chimeric or hybrid antibodies with dual or multiple antigen or epitope specificities. It can be a polyclonal antibody, preferably an affinity-purified antibody from a human or an appropriate animal, e.g., a primate, goat, rabbit, mouse or the like. Monoclonal antibodies are also suitable for use in the present invention, and are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility in the present invention. It will be appreciated that newer techniques for production of monoclonals can also be used, e.g., human monoclonals, interspecies monoclonals, chimeric (e.g., human/mouse) monoclonals, genetically engineered antibodies and the like.

Antibody fragments useful in the present invention include $F(ab')_2$, $F(ab)_2$, Fab', Fab, Fv and the like including hybrid fragments. Preferred fragments are Fab', $F(ab')_2$, Fab, and $F(ab)_2$. Also useful are any subfragments retaining the hypervariable, antigen-binding region of an immunoglobulin and having a size similar to or smaller than a Fab' fragment. This will include genetically engineered and/or recombinant proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of $F(ab')_2$ fragments, which themselves may be made by pepsin digestion of intact immunoglobulin. Fab antibody fragments may be made by papain digestion of intact immunoglobulin, under reducing conditions, or by cleavage of $F(ab)_2$ fragments which result from careful papain digestion of whole immunoglobulin. The fragments may also be produced by genetic engineering.

It should be noted that mixtures of antibodies and immunoglobulin classes can be used, as can hybrid antibodies. Multispecific, including bispecific and hybrid, antibodies and antibody fragments are especially preferred in the methods of the present invention for detecting and treating lesions and are comprised of at least two different substantially monospecific antibodies or antibody fragments, wherein at least two of said antibodies or antibody fragments specifically bind to at least two different antigens produced or associated with the targeted lesion or at least two different epitopes or molecules of a marker substance produced or associated with the targeted lesion. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., *Immunol. Today,* 5,299(1984).

Preferred are proteins having a specific immunoreactivity to a marker substance of at least 60% and a cross-reactivity to other antigens or non-targeted substances of less than 35%.

As disclosed above, antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alia, in U.S. Pat. Nos. 3,927,193 to Hanson et al. and 4,331,647, 4,348,376, 4,361,544, 4,468,457, 4,444,744, 4,818,709 and 4,624,846 to Goldenberg. In particular, antibodies against an antigen, e.g., a gastrointestinal, lung, breast, prostate, ovarian, testicular, brain or lymphatic tumor, a sarcoma or a melanoma, are advantageously used.

A wide variety of monoclonal antibodies against infectious disease agents have been developed, and are summarized in a review by Polin, in *Eur. J. Clin. Microbiol.,* 3(5):387–398, 1984, showing ready availability. These include monoclonal antibodies (MAbs) against pathogens and their antigens such as the following:

Anti-bacterial Mabs
*Streptococcus agalactiae*
*Legionella pneumophilia*
*Streptococcus pyogenes*
*Escherichia coli*
*Neisseria gonorrhosae*
*Neisseria meningitidis*
Pneumococcus
*Hemophilis influenzae* B
*Treponema pallidum*
Lyme disease spirochetes
*Pseudomonas aeruginosa*
*Mycobacterium leprae*
*Brucella abortus*
*Mycobacterium tuberculosis*
Tetanus toxin
Anti-viral MAbs
HIV-1, -2, -3
Hepatitis A, B, C, D Rabies virus
Influenza virus
Cytomegalovirus
Herpes simplex I and II
Human serum parvo-like virus
Respiratory syncytial virus
Varicella-Zoster virus
Hepatitis B virus
Measles virus
Adenovirus
Human T-cell leukemia viruses
Epstein-Barr virus
Murine leukemia virus*
Mumps virus
Vesicular stomatitis virus
Sindbis virus
Lymphocytic choriomeningitis virus
Wart virus
Blue tongue virus
Sendai virus
Feline leukemia virus*
Reo virus
Polio virus
Simian virus 40*
Mouse mammary tumor virus*
Dengue virus
Rubella virus
*=animal virus Anti-protozoan MAbs
*Plasmodium falciparum*
*Plasmodium vivax*
*Toxoplasma gondii*
*Trypanosoma rangeli*
*Trypanosoma cruzi*
*Trypanosoma rhodesiensei*
*Trypanosoma brucei*
*Schistosoma mansoni*
*Schistosoma japanicum*
*Babesia bovis*
*Elmeria tenella*
*Onchocerca volvulus*
*Leishmania tropica*
*Trichinella spiralis*
*Theileria parva*
*Taenia hydatigena*
*Taenia ovis*
*Taenia saginata*
*Echinococcus granulosus*
*Mesocestoides corti*

Antimycoplasmal MAbs
*Mycoplasma arthritidis*
*M. hyorhinis*
*M. orale*
*M. arginini*
*Acholeplasma laidlawii*
*M. salivarium*
*M. pneumoniae*

Additional examples of MAbs generated against infectious organisms that have been described in the literature are noted below.

MAbs against the gp120 glycoprotein antigen of human immunodeficiency virus 1 (HIV-1) are known, and certain of such antibodies can have an immunoprotective role in humans. See, e.g., Rossi et al., Proc. Natl. Acad. Sci. USA, 86:8055–8058, 1990. Other MAbs against viral antigens and viral induced antigens are also known. This shows that proper selection of the epitope can distinguish between a therapeutic and non-therapeutic target.

MAbs against malaria parasites can be directed against the sporozoite, merozoite, schizont and gametocyte stages. Monoclonal antibodies have been generated against sporozoites (circumsporozoite antigen), and have been shown to neutralize sporozoites in vitro and in rodents (N. Yoshida et al., *Science* 207:71–73, 1980).

Several groups have developed MAbs to *T. gondii*, the protozoan parasite involved in toxoplasmosis (Kasper et al., *J. Immunol.* 129:1694–1699, 1982; Id., 130:2407–2412, 1983).

MAbs have been developed against schistosomular surface antigens and have been found to act against schistosomulae in vivo or in vitro (Simpson et al., *Parasitology,* 83:163–177, 1981; Smith et al., *Parasitology,* 84:83–91, 1982; Gryzch et al., *J. Immunol.,* 129:2739–2743, 1982; Zodda et al., *J. Immunol.* 129:2326–2328, 1982; Dissous et al., *J. Immunol.,* 129:2232–2234, 1982).

*Trypanosoma cruzi* is the causative agent of Chagas' disease, and is transmitted by blood-sucking reduviid insects. A MAb has been generated that specifically inhibits the differentiation of one form of the parasite to another (epimastigote to trypomastigote stage) in vitro, and which reacts with a cell-surface glycoprotein; however, this antigen is absent from the mammalian (bloodstream) forms of the parasite (Sher et al., *Nature,* 300:639–640, 1982).

Suitable MAbs have been developed against most of the microorganisms (bacteria, viruses, protozoa, other parasites) responsible for the majority of infections in humans, and many have been used previously for in vitro diagnostic purposes. These antibodies, and newer MAbs that can be generated by conventional methods, are appropriate for use in the present invention.

Proteins useful for detecting and treating cardiovascular lesions include fibrin-specific proteins, for example, fibringen, soluble fibrin, antifibrin antibodies and fragments, fragment $E_1$ (a 60 kDa fragment of human fibrin made by controlled plasmin digestion of crosslinked fibrin), plasmin (an enzyme in the blood responsible for the dissolution of fresh thrombi), plasminogen activators (e.g., urokinase, streptokinase and tissue plasminogen activator), heparin, and fibronectin (an adhesive plasma glycoprotein of 450 kDa) and platelet-directed proteins, for example, platelets, antiplatelet antibodies and antibody fragments, anti-activated platelet antibodies, and anti-activated-platelet factors, which have been reviewed by Koblik et al., *Semin. Nucl. Med.,* 19:221–237 1989, all of which is included herein by reference.

Among the radionuclides and labels useful in the methods of the present invention, gamma-emitters, positron-emitters, x-ray emitters and fluorescence-emitters are suitable for localization and/or therapy, while beta- and alpha-emitters and electron- and neutron-capturing agents, such as boron and uranium, also can be used for therapy.

The loading of metallic radioisotopes into biotin or avidin/chelating protein conjugates and the use of such radioimmunoconjugates in pre-targeted radioimmunotherapy has implications in isotope choice for this modality.

Firstly, the extended serum half-life of, for example, ferritin derivatives may dictate the use of isotopes of longer physical half-life, particularly if a human ferritin is used in the clinical setting.

Secondly, the use of a carrier with a high loading capability, means that radionuclides with a lower specific activity can now be considered as viable radioimmunotherapy agents. With ferritin particularly, because of its exceptional high payload potential, the use of a carrier-added isotopes becomes more practicable. As an example, a human biotin-ferritin will probably not elicit any immune reaction and can be expected to circulate for an extended period. It can essentially be expected to behave like a time-release capsule slowly and steadily localizing at the target site. The implication of this may be to use an isotope of shorter range in tissue (lower decay energy) and longer half-life to both spare blood and marrow cells while delivering a sustained dose-level to the target. The methodology used in this approach, in essence, allows the choice of possible radiotherapeutic isotopes to be expanded considerably.

Suitable radioisotopes for the methods of the present invention include: Actinium-225, Bismuth-210, Bismuth-212, Erbium-169, Indium-111, Indium-113m, Gallium-67, Gallium-68, Osmium-191, Neodymium-147, Ruthenium-95, Ruthenium97, Ruthenium-103, Ruthenium-105, Mercury-107, Mercury-203, Rhenium-186, Rhenium-188, Rhenium-189, Tellurium-121m, Tellurium-122m, Tellurium-125m, Thulium-165, Thulium-167, Thulium-168, Technetium-99m, Tungsten-189,Tungsten188, Silver-111, Platinum-197, Palladium-109, Copper-67, Yttrium-90, Scandium-47, Samarium-153, Lutetium-177, Rhodium-105, Praseodymium-142, Praseodymium-143, Terbium-161, Holmium-166, Gold-199, Cadmium-115m, Cerium-141, Radium-223, Radium-225, Tantalum-183, Thorium-234, Uranium-230, Uranium-237, Cobalt-57, Cobalt-58, Chromium-51, Iron-59, Thallium-201, Ytterbium-169 and Ytterbium-175. Preferably the radioisotope will emit in the 10–7,000 kev range, more preferably 50–1,500 kev, most preferably 50–500 kev.

Isotopes preferred for external imaging include: Indium-111, Gallium-67, Ruthenium-97, Technetium-99m, Cobalt-57, Cobalt-58, Chromium-51, Iron-59, Thallium-201, and Ytterbium-169.

Isotopes most preferred for internal detection include: Indium-Ill, Technetium-99m and Gallium-67.

Isotopes preferred for therapeutic use include: Rhenium-186, Rhenium-188, Rhenium-189, Silver-111, Platinum-197, Palladium-109, Copper-67, Yttrium-90, Scandium-47, Samarium-153, Lutetium-177, Rhodium-105, Praseodymium-142, Praseodymium-143, Terbium-161, Holmium-166, and Gold-199.

Isotopes preferred for therapeutic use when chelated by ferritin include Ruthenium-103, Silver-111, Cadmium-115m, Cerium-141, Praseodymium-143, Neodymium-147, Terbium-161, Erbium-169, Ytterbium-175, Lutetium-177, Tantalum-183, Tungsten-185, Tungstem-188, Rhenium-186, Osmium-191, Bismuth-210, Radium-223, Radium-225, Actinium-225, Thorium-234, Uranium-230, and Uranium-237.

Many drugs are known which have cytotoxic effects on cells. They are to be found in compendia of drugs and toxins, such as the Merck Index, Goodman and Gilman, and the like, and in the references cited above. Cytotoxic drugs capable of being chelated are known to those skilled in the art and are useful in the methods of the present invention.

Biotin can be readily conjugated to proteins (including antibodies and their fragments) by methods known in the art by using the proteins' lysine and cysteine residues and, if available, their oxidized carbohydrate groups.

The prior art teaches many methods for conjugating chelating protein to avidin or biotin. Several of the methods are exemplified in the Examples herein.

Hainfield, PNAS, USA, 89:11068, 1992 discloses one method of biotinating ferritin. In the Hainfield method apoferritin is loaded with approximately 800 atoms of uranium and conjugated to MAb with the aim of performing uranium neutron-capture therapy. This method can be used to chelate metals, such as, uranium, iron, gadolinium, chromium and manganese.

The biotinylation of metallothionein can be performed through thio- or amino-groups on the protein. The presence of available free thiols on metallothionein negates the need for a reduction step as needed in the apoferritin modification. The need for free thiols to be present to bind metal ions requires the use of a limiting amount of biotinylated derivative to be used when the thiol groups are targeted for biotinylation.

One method for biotinylation of thiol (sulfhydryl) groups, is to treat a solution of metallothionein in acetate, phosphate, or citrate buffer, pH 5–8, with a one-tenth to one-sixth molar amount of N-biotinyl-N'-(6-maleimidohexanoyl)hydrazide for 0.25 to 24 hours at 4–37° C. The biotinylated metallothionein is then purified from the unreacted biotin by dialysis and/or size-exclusion chromatography and the biotin substitution ratio determined using HABA as shown in the Examples. Substitution of biotin onto amino-groups requires protection of the free thiol groups prior to biotinylation, with acylation and oxidation as the preferred methods. For the latter, a 0.01–10 mmol solution of metallothionein is treated with small amounts of dilute hydrogen peroxide until assay for free thiol groups by the Ellman reaction (*Arch. Biochem. Biophys.* 82:70–77, 1959) is negative. The thiol-protected metallothionein is then reacted with N-hydroxysulfosuccinimidylbiotin under conditions similar to the above amino-group biotinylation of apoferritin. The biotinylated metallothionein is then purified and analyzed for substitution ratio as described above. A known concentration of oxidized biotinylated-metallothionein is then treated with a 0.01–100 mmol solution of sodium borohydride for 0.25–24 h at 4–37° to reliberate the free thiol groups. The course of the deprotection reaction is followed by the Ellman reaction to determine the time of complete reaction.

A physiological solution of the conjugate of biotin or avidin and chelating protein conjugate is advantageously metered into sterile vials, e.g., at a unit dosage of about 1.0–500 mg of the conjugate, and the vials are either stoppered, sealed and stored at low temperature, or lyophilized, stoppered, sealed and stored. The vials are reconstitution with a solution containing the metal to be chelated with the chelating protein.

Variations and modifications of the formulations will be readily apparent to the ordinary skilled artisan, as a function of the individual needs of the patient or treatment regimen, as well as of variations in the form in which the radioisotopes may be provided or may become available.

In an embodiment of the improved detection or therapeutic protocol of the present invention, the biotin-targeting protein can be injected parenterally, usually at a protein dose of 0.5 to 50 mg. This can be administered as a single injection or in divided doses. After 1–5 days, more preferably at less than 2 days and even at less than 1 day when the first agent involves a small and rapidly targeting molecule, such as an antibody fragment or subfragment, a dose of unlabeled clearing agent, such as 2.0 to 200.0 mg avidin is administered parenterally. The clearing agent can be given as a single injection or in divided doses, wherein administering the clearing agent in 2 doses is preferred in certain circumstances. The third step involves injection of the conjugate of biotin, chelating protein and detection or therapeutic metal. The third step's reagents can be administered parenterally within 24 hours of the 2nd step, but also at up to 3 days later. In one detection embodiment, the third step involves Tc-99m bound by metallothionein multiply substituted with biotin. Within 24 hrs of the last injection, more preferably within 4 hrs, planar and single-photon emission computed tomography scans are made with a gamma camera equipped with the appropriate collimator and selecting the appropriate energy windows for the detection isotope being used.

Routes of administration include intravenous, intraarterial, intrapleural, intraperitoneal, intrathecal, subcutaneous or by perfusion.

An application of the lesion-specific or lesion-associated protein disclosed hereinabove is for magnetic resonance imaging (MRI). In this case, for example, an antibody/fragment bearing a MR image enhancing agent is administered with the intention of obtaining an image of the lesion.

The method of the invention can be practiced either with scintigraphic or magnetic resonance imaging agents. A combination of these imaging agents can also be used, although this requires more complex instrumentation and data processing.

Scintigraphic imaging according to the method of the invention is effected by obtaining a scintigram of the lesion of interest.

The scintigram is normally taken by a gamma imaging camera having one or more windows for detection of energies in the 50–500 keV range. Use of radioisotopes with higher energy, beta, or positron emissions would entail use of imaging cameras with the appropriate detectors, all of which are conventional in the art.

The scintigraphic data can be stored in a computer for later processing.

Methods useful for internal detection and/or treatment of tumors and/or other lesions are disclosed in U.S. Pat. Nos. 4,782,840; 4,932,412; and copending U.S. application Ser. No. 07/879,857, the disclosures of which are incorporated herein by reference. The methods of the present invention can be used to enhance the methods disclosed in these references.

Magnetic resonance imaging (MRI) is effected in an analogous manner to scintigraphic imaging except that the imaging agents will contain magnetic resonance (MR) enhancing species rather than radioisotopes. It will be appreciated that the magnetic resonance phenomenon operates on a different principle from scintigraphy. Normally, the signal generated is correlated with the relaxation times of the magnetic moments of protons in the nuclei of the hydrogen atoms of water molecules in the region to be imaged. The magnetic resonance image enhancing agent acts by increasing the rate of relaxation, thereby increasing the contrast between water molecules in the region where the imaging agent accretes and water molecules elsewhere in the body. However, the effect of the agent is to decrease both $T_1$ and $T_2$, the former resulting in greater contrast while the latter results in lesser contrast. Accordingly, the phenomenon is concentration-dependent, and there is normally an optimum concentration of a paramagnetic species for maximum efficacy. This optimal concentration will vary with the particular agent used, the locus of imaging, the mode of imaging, i.e., spin-echo, saturation-recovery, inversion-recovery and/or various other strongly $T_1$-dependent or $T_2$-dependent imaging techniques, and the composition of the medium in which the agent is dissolved or suspended. These factors, and their relative importance are known in the art. See, e.g., Pykett, *Scientific American,* 246, 78(1982); Runge et al., *Am. J. Radiol,* 141, 1209 (1983).

The MR image enhancing agent must be present in sufficient amounts to enable detection by an external camera, using magnetic field strengths which are reasonably attainable and compatible with patient safety and instrumental design. The requirements for such agents are well known in the art for those agents which have their effect upon water molecules in the medium, and are disclosed, inter alia, in Pykett, op. cit., and Runge et al., op. cit.

Preparation of chelating protein chelated to a magnetic resonance image enhancing agent can be effected by a variety of methods known in the art.

MRI contrast agents are well known in the art and include, for example, Gadolinium, Iron, Manganese, Rhenium, Europium, Lanthanium, Holmium, and Terbium.

The MR scans are stored in a computer and the images processed analogously to the scintigraphic data.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Accordingly, these embodiments constitute improved methods and reagents for amplification of protein, especially antibody and antibody fragments, targeting for detecting and therapy of cancer and other pathological conditions.

EXAMPLES

Example 1

Conjugating Targeting Antibody or Antibody Fragment to Biotin

A—Via Lysin.

An antibody at a concentration of 10 mg/ml in a borate buffer, 0.1M, pH 8.5 is mixed with a 10 fold molar excess of the activated sulfosuccinimide ester of D-biotin. The reaction solution is stirred for 16 hours and kept at a temperature of 25° C. At the end of the reaction period, the modified protein is separated from unbound biotin and other low molecular weight contaminants by size-exclusion chromatography on a G-25 Sephadex column.

B—Via Cysteine.

An antibody fragment at a concentration of 10 mg/ml in 0.2M tris buffer, pH 8.7, is made 2 mg/ml in 2-mercaptoethanol. The reaction solution is let stand 10 minutes at a temperature of 4° C. The reduced protein is separated from unreacted thiol by size-exclusion chromatography in 50 mM acetate buffer, pH 4.5. Protein concentration and the number of thiol groups per antibody molecule are determined at this time. The reduced antibody at a concentration of 10 mg/ml in a phosphate buffer, pH 7.5 is mixed with a 10 fold molar excess of biotin-maleimide (N-biotinyl-N[6-maleimido hexanoyl]hydrazide) (Sigma Chem. Co). A co-solvent of DMSO, is added to provide a final concentration of up to 20% to facilitate reactant solubility. The reaction solution is stirred for 6 hours at a temperature between 37° C. At the end of the reaction period, the biotinylated protein is separated from unbound biotin and other low molecular weight contaminants by size-exclusion chromatography on a G-25 Sephadex column.

C—Via a Carbohydrate.

Antibody at a concentration of 10 mg/ml is treated with sodium metaperiodate to a final concentration of 0.3 mg/ml in phosphate buffered saline at room temperature for 4 hours. Ethylene glycol is added to decompose the remaining periodate. The oxidized IgG is purified from low molecular weight contaminants by size-exclusion chromatography in phosphate buffer, 0.1M, pH 7.5. The oxidized antibody (10 mg/ml) is reacted with a 10 molar excess of biotin-hydrazide (Pierce Chemical Co.) in a phosphate buffer, pH 7.5, 0.1M for 6 hours at 37° C. After coupling, the formed hydrazones are reduced by the addition of 0.2 mmol of sodium cyanoborohydride with stirring overnight. The biotinylated antibody is purified by size-exclusion chromatography on a G-25 Sephedex column.

D—Via addended Thiol Groups

An antibody fragment at a concentration of 10 mg/nil in a phosphate buffer 0.1M pH 8 is mixed with a 5 fold molar excess of 2-iminothiolane hydrochloride (Pierce Chemical Co.). The reaction mixture is made 2 mM in EDTA to help prevent disulfide bond formation and held at 4° for 4 hours. The modified protein is purified by size-exclusion chromatography in 0.1M acetate buffer, pH 5.0. The purified sulfhydryl substituted antibody (1–20 mg/nil) is mixed, at a pH of 7.5 in 0.1M phosphate buffer, with a 1 fold molar excess of biotin maleimide. A co-solvent, DMSO, is added to a final concentration of 10% to facilitate reactant solubility. The reaction solution is stirred for 24 hours at a temperature of 25° C. At the end of the reaction period, the biotinylated protein is separated from unbound biotin and other low molecular weight contaminants by size-exclusion chromatography on a G-25 Sephadex column.

Example 2

Conjugating Biotin and Targeting Fab' Fragments

An antibody $F(ab')_2$ fragment (obtained by pepsin digestion of the intact antibody) at a concentration of 20 mg/ml in phosphate buffer at pH 7 is treated with a freshly prepared solution of L-cysteine to give a final cysteine concentration of 25 mg/ml. The reaction is allowed to proceed for 1.5 hours at 37° C. At the end of this period, the Fab' fragment is purified from low molecular weight contaminants by size-exclusion chromatography in 0.1M acetate buffer at pH 4.0. The Fab' fragment is reacted with a 5 fold molar excess of biotin-maleimide at pH 7.0. A co-solvent, DMSO, is added to a final concentration 10% to facilitate reactant solubility. The reaction is stirred for 4 hours at a temperature of 25° C. At the end of the reaction period, the biotinylated antibody fragment is separated from unbound biotin and other low molecular weight contaminants by size-exclusion chromatography on a G-25 sephadex column.

Example 3

Determination of Extent of Biotinylation of Targeting Proteins

A small amount of biotinylated protein is heated to 56° in 0.1M phosphate buffer for 10 minutes and enzymatically digested with small volumes of 1% pronase (Sigma Chemical Co.). The digestion is allowed to proceed overnight. The digest is analyzed with a 10 μM solution of avidin saturated with a 100 μM solution of 2-(4'-hydroxyazobenzene)-benzoic acid (HABA) in 0.1M phosphate buffer, pH 7.0. The avidin-HABA solution is titrated with increasing volumes of digested biotinylated antibody as well as a standard biotin solution containing 1–10 mM of biotin. The change in absorbance at 500 nM for each is determined, and the concentration of biotin in the pronase digested biotinylated antibody calculated from reference to the standard curve of the titration of biotin with avidin-HABA.

Example 4

Conjugating Ferritin to Biotin (a) Via amino-groups on the protein.

A 0.1 μmol to 0.1 mmol solution of apoferritin in phosphate buffer (0. 1 mol, pH 8) is treated with a solution of N-hydroxysulfosuccinimidylbiotin and reacted for 16 hours at room temperature. The protein is purified from unreacted biotin by a size exclusion column. The number of biotin residues incorporated per ferritin can be determined using 2-(4'-hydroxyazobenzene)benzoic acid (HABA) reagent (Green, *Biochem. J.* 94:23c–24c, 1965), as described in the previous example.

(b) Via sulfhydryl-groups on the protein.

A solution of the protein in tris buffer (0.2 mol, pH 7.5) is treated with 2-mercaptoethanol (2 mmol) for 1 hour at 4° C. After purification of protein from unreacted biotin on size-exclusion chromatography, the biotin substitution level is determined as above in example 6.

Example 5

Chelating Metal Into Biotin-Apoferritin

The incorporation of gadolinium into biotinyl-apoferritin is modeled on the loading of uranium into apoferritin (Hainfeld, PNAS USA, 89:11064–11068, 1992). Briefly, each biotinyl-apoferritin is treated with a 0.01–1 mol solution of gadolinium cation in phosphate, citrate or acetate buffer at a pH of 3–7 for 0.5–24 h at 4–37° C. The metalated biotinyl-apoferritin is separated from unincorporated metal by dialysis and/or size-exclusion chromatography.

Example 6

Chelating Metal Into Biotin-Metallothionein Conjugate

The biotinylated metallothionein is metallated by incubation of the biotin-metallothionein conjugate with the metal of interest in a suitable buffer system, typically in the pH range of 3–12 for a time of 0.25–24 h. For metals expected to bind to sulfhydryl groups when they are in a lower oxidation state (for example rhenium, gold, manganese and copper among others), a reductant such as stannous ion, sodium borohydride or hydrazine may be added to the metalation mixture. Alternatively, metals such as these may be pre-reduced prior to addition to the biotin-metallothionein polymer. Metalated protein may be purified from unbound metal by dialysis and/or size-exclusive/ion-exchange chromatography. The ratio of incorporated metal into biotin-metallothionein may be determined by atomic absorption spectroscopy or other spectrophotometric methods tailored to individual metals.

Example 7

Cancer Imaging With Three-Step Procedure

A patient diagnosed by sigmoidoscopy to have a colonic neoplasm is injected i.v. with a biotin-monoclonal antibody IgG against carcinoembryonic antigen (CEA). Two days later, unlabeled avidin (in two divided doses, 20 min apart) is injected i.v. The next day, biotin-metallothionein-Tc99m conjugate is injected i.v. The patient is scanned with a gamma camera 2 hours later, and the neoplasm is readily distinguished over background activity.

Example 8

Cancer Radioimmunotherapy Procedure

A patient with several small colonic carcinoma metastases to the liver, which have been imaged and localized, is injected i.v. with a dose of a first composition comprised of a conjugate of avidin-anti-CEA IgG monoclonal antibody. Two days later, a clearing and localizing multi-biotin composition of biotin is injected i.v. (in two divided doses, 30 min apart). After another 2 days, a dose of a composition of avidin-ferritin-uranium is injected i.v. A collimated slow neutron beam is directed at the previously imaged sites of metastasis, the dosimetry being adjusted suitably as a function of the uranium metal ion loading, the irradiation being optionally delivered in sequential doses over several days. Within a week of the initial neutron irradiation, radioimmunodetection shows significant reduction in the size of the tumors.

The preceding examples can be repeated with similar success by substituting the generically or specifically described reactants and/or operating conditions of this invention for those used in the preceding examples.

From the foregoing descriptions, one skilled in the art can easily ascertain the essential characteristics of this invention and, without departing from the spirit and scope thereof, can make various changes and modifications of the invention to adapt it to various usages and conditions.

We claim:

1. A method of detecting or treating lesions in a patient, the method comprising the steps of:

(a) injecting a patient with a first composition comprised of a conjugate of biotin and a non-antibody targeting protein, wherein the targeting protein preferentially binds to a marker substance produced by or associated with the target lesion, and allowing the biotin-targeting protein conjugate to accumulate at the target lesion;

(b) injecting at least one dose of a clearing and localizing agent comprised of avidin, and allowing the agent to remove circulating biotin-targeting protein conjugate and to localize at the targeted lesion by binding to biotin at the target lesion;

(c) injecting a composition comprised of a conjugate of biotin and a naturally occurring metal atom chelating protein chelated with a chelatable metal detection or therapeutic agent, and allowing the conjugate to bind to the avidin accumulated at the targeted lesion; and (d) using the detection or therapeutic agent to detect or treat the targeted lesion.

2. A method of detecting or treating lesions in a patient, the method comprising the steps of:

(a) injecting a patient with a first composition comprised of a conjugate of avidin and non-antibody targeting protein, wherein the targeting protein preferentially binds to a marker substance produced by or associated with the target lesion, and allowing the conjugate to accumulate at the target lesion;

(b) optionally, injecting a clearing agent comprised of biotin, and allowing the clearing agent to remove circulating avidin-protein conjugate;

(c) injecting a localizing composition comprised of a conjugate containing multiple biotin molecules, and allowing the multi-biotin conjugate to bind to avidin accumulated at the target lesion;

(d) injecting a composition comprised of a conjugate of avidin and naturally occurring metal-ion chelating protein chelated with a chelatable metal detection or therapeutic agent, and allowing the conjugate to bind to the biotin at the targeted lesion; and (e) using the detection or therapeutic agent to detect or treat the targeted lesion.

3. A method of detecting or treating lesions in a patient, the method comprising the steps of:

(a) injecting a patient with a first composition comprised of a conjugate of avidin and non-antibody targeting protein, wherein the targeting protein preferentially binds to a marker substance produced by or associated with the target lesion, and allowing the avidin-targeting protein conjugate to accumulate at the target lesion;

(b) optionally, injecting a clearing agent comprised of biotin, and allowing the clearing agent to remove circulating avidin-targeting protein conjugate;

(c) injecting a composition comprised of a conjugate of biotin and naturally occurring metal-ion chelating protein chelated with chelatable metal detection or therapeutic agent, and allowing the conjugate to bind to the avidin accumulated at the targeted lesion; and (d) using the detection or therapeutic agent to detect or treat the targeted lesion.

4. The method of claim 1, wherein the lesion is cancerous, cardiovascular, infectious or inflammatory.

5. The method of claim 4, wherein the lesion is a cardiovascular lesion selected from the group consisting of a thrombus, embolus, infarct and atherosclerotic plaque.

6. The method of claim 4, wherein the lesion is a cancerous lesion selected from the group consisting of a carcinoma, melanoma, sarcoma, neuroblastoma, leukemia, lymphoma, glioma, myeloma and neural tumor.

7. The method of claim 1, wherein the method is for external imaging of a lesion, and wherein the detection agent is an imaging radionuclide or an MRI image-enhancing agent.

8. The method of claim 1, wherein the method is for internal direct detection of a lesion during an operative, intravascular or endoscopic procedure.

9. The method of claim 1, wherein the method is for treating a lesion, and wherein the therapeutic agent is a therapeutic radioisotope.

10. The method of claim 1, wherein the method is for treating a lesion, and wherein the therapeutic agent is an electron- or neutron-capturing agent.

11. The method of claim 9, wherein the isotope is Actinium-225, Rhenium-186, Rhenium-188, Rhenium189, Silver-111, Platinum-197, Palladium-109, Copper-67, Yttrium-90, Scandium 47, Samarium-153, Lutetium-177, Rhodium-105, Praseodymium-142, Praseodymium-143, Terbium-161, Holmium-166, or Gold-199.

12. The method of claim 1, wherein the naturally occurring chelating protein is a ferritin, metalothionein, ferredoxin, nitrogenase, ceruloplasmin or laccase.

13. The method of claim 12, wherein the naturally occurring chelating protein is ferritin.

14. The method of claim 2, wherein the lesion is cancerous, cardiovascular, infectious or inflammatory.

15. The method of claim 3, wherein the targeting protein is a polypeptide selected from the group consisting of a hormone, growth factor, cytokine, enzyme, immune modulator, receptor protein and non-antibody anti-receptor protein.

16. The method of claim 2, wherein the method is for external imaging of a lesion, and wherein the detection agent is an imaging radionuclide or an MRI image-enhancing agent.

17. The method of claim 2, wherein the method is for internal direct detection of a lesion during an operative, intravascular or endoscopic procedure.

18. The method of claim 2, wherein the method is for treating a lesion, and wherein the therapeutic agent is a therapeutic radioisotope.

19. The method of claim 2, wherein the method is for treating a lesion, and wherein the therapeutic agent is an electron- or neutron-capturing agent.

20. The method of claim 2, wherein the naturally occurring chelating protein is a ferritin, metalothionein, ferredoxin, nitrogenase, ceruloplasmin or laccase.

21. The method of claim 20, wherein the naturally occurring chelating protein is ferritin.

22. The method of claim 3, wherein the lesion is cancerous, cardiovascular, infectious or inflammatory.

23. The method of claim 4, wherein the targeting protein is a polypeptide selected from the group consisting of a hormone, growth factor, cytokine, enzyme, immune modulator, receptor protein and non-antibody anti-receptor protein.

24. The method of claim 3, wherein the method is for external imaging of a lesion, and wherein the detection agent is an imaging radionuclide or an MRI image-enhancing agent.

25. The method of claim 3, wherein the method is for internal direct detection of a lesion during an operative, intravascular or endoscopic procedure.

26. The method of claim 3, wherein the method is for treating a lesion, and wherein the therapeutic agent is a therapeutic radioisotope.

27. The method of claim 3, wherein the method is for treating a lesion, and wherein the therapeutic agent is an electron- or neutron-capturing agent.

28. The method of claim 3, wherein the naturally occurring chelating protein is a ferritin, metalothionein, ferredoxin, nitrogenase, ceruloplasmin or laccase.

29. The method of claim 28, wherein the naturally occurring chelating protein is ferritin.

30. The method of claim 1, wherein the targeting protein is selected from the group consisting of hormones, growth factors, cytokines, enzymes, immune modulators, receptor proteins, and non-antibody anti-receptor proteins.

31. The method of claim 1, wherein the targeting protein is selected from the group consisting of fibrinogen, soluble fibrin, fragment $E_1$, plasmin, plasminogen activators, heparin, fibronectin, platelets and non-antibody proteins that bind activated platelet factors.

32. The method of claim 2, wherein the targeting protein is selected from the group consisting of fibrinogen, soluble fibrin, fragment $E_1$, plasmin, plasminogen activators, heparin, fibronectin, platelets and non-antibody proteins that bind activated platelet factors.

33. The method of claim 3, wherein the targeting protein is selected from the group consisting of fibrinogen, soluble fibrin, fragment $E_1$, plasmin, plasminogen activators, heparin, fibronectin, platelets and non-antibody proteins that bind activated platelet factors.

34. The method of claim 1, wherein the naturally occurring metal atom chelating protein has a molecular weight of at least about 60,000 daltons.

35. The method of claim 2, wherein the naturally occurring metal atom chelating protein has a molecular weight of at least about 60,000 daltons.

36. The method of claim 3, wherein the naturally occurring metal atom chelating protein has a molecular weight of at least about 60,000 daltons.

* * * * *